United States Patent
Jonas et al.

(10) Patent No.: US 7,259,168 B2
(45) Date of Patent: Aug. 21, 2007

(54) 2-AMINOALKYL-THIENO[2,3-D] PYRIMIDINES

(75) Inventors: Rochus Jonas, Darmstadt (DE); Pierre Schelling, Muehltal (DE); Maria Christadler, Roedermark (DE); Norbert Beier, Reinheim (DE)

(73) Assignee: Merck Patent GmbH, Darmstadt (DE)

( * ) Notice: Subject to any disclaimer, the term of this patent is extended or adjusted under 35 U.S.C. 154(b) by 666 days.

(21) Appl. No.: 10/312,767

(22) PCT Filed: Jun. 28, 2001

(86) PCT No.: PCT/EP01/07379

§ 371 (c)(1),
(2), (4) Date: Sep. 16, 2003

(87) PCT Pub. No.: WO02/00664

PCT Pub. Date: Jan. 3, 2002

(65) Prior Publication Data
US 2004/0044011 A1    Mar. 4, 2004

(30) Foreign Application Priority Data
Jun. 29, 2000   (DE) ............... 100 31 585

(51) Int. Cl.
*A01N 43/90* (2006.01)
(52) U.S. Cl. .................... 514/260.1; 514/260
(58) Field of Classification Search ............ 514/260.1, 514/262.1
See application file for complete search history.

(56) References Cited

U.S. PATENT DOCUMENTS

| | | | |
|---|---|---|---|
| 6,110,920 A * | 8/2000 | Rochus et al. ........... 514/260.1 |
| 6,130,223 A | 10/2000 | Janas et al. | |
| 8,777,419 | 8/2004 | Rochus et al. | |
| 6,787,548 B1 * | 9/2004 | Jonas et al. .................. 514/250 |
| 2003/0022906 A1 * | 1/2003 | Brandle et al. ............. 514/267 |
| 2004/0029900 A1 * | 2/2004 | Jonas et al. .............. 514/262.1 |
| 2004/0044011 A1 * | 3/2004 | Jonas et al. .............. 514/260.1 |

FOREIGN PATENT DOCUMENTS

WO    WO94/28902    12/1994

OTHER PUBLICATIONS

Takase et al., J.Med.Chem, 36, p. 3765+ (1993).
Takase et al., J.Med.Chem, 37, p. 2106+ (1994).

* cited by examiner

*Primary Examiner*—Thurman K. Page
*Assistant Examiner*—MLouisa Lao
(74) *Attorney, Agent, or Firm*—Millen, White, Zelano & Branigan, P.C.

(57) ABSTRACT

The present invention relates to 2-aminomethylthieno[2,3-d]pyrimidines of the general formula (I)

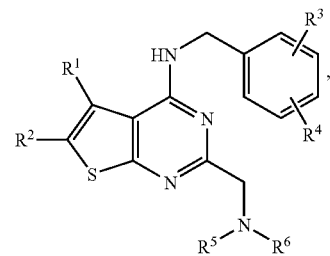

in which the radicals $R^1$ to $R^6$ have the meaning indicated in the text. The compounds show phosphodiesterase V inhibition and can be employed for the treatment of conditions of the cardiovascular system and for the treatment of potency disorders.

8 Claims, No Drawings

2-AMINOALKYL-THIENO[2,3-D]PYRIMIDINES

The present invention relates to 2-aminoalkylthieno[2,3-d]pyrimidines of the general formula (I)

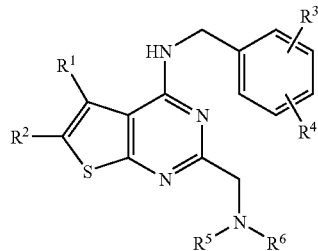

I in which the radicals $R^1$ to $R^6$ have the meaning indicated in the text, and to their use as medicaments, in particular as c-GMP phosphodiesterase inhibitors.

Substances having c-GMP phosphodiesterase-inhibiting properties have been known for a number of years. If the cyclo-guanosine monophosphate (c-GMP) level is pathologically raised, they serve to lower it. By means of this, the symptoms occurring in the case of a raised c-GMP level, such as inhibition and prevention of inflammation, and muscle relaxation are suppressed or prevented. c-GMP phosphodiesterase inhibitors are used in particular for the treatment of cardiovascular diseases and of potency disorders.

There are various molecular compound classes which are known for their c-GMP phosphodiesterase-inhibiting properties.

These are, on the one hand, quinazolines, which are described, for example, in J. Med. Chem. 36, page 3765 ff (1993) and in J. Med. Chem. 37, page 7106 ff (1994).

On the other hand, pyrazolopyrimidones which are described in WO 94/28902 are also suitable. The use of the class of substance for the treatment of impotence is also disclosed here.

The use of pyrazolo[4,3-d]pyrimidines for the treatment of cardiovascular conditions and impotence is disclosed in the German application having the reference 199 42 474.8.

Finally, in the German application having the reference 196 44 228.1 the use of thienopyrimidines having the general formula

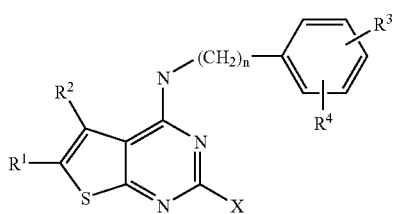

II is described. The substituents $R^1$ to $R^4$ here are various alkyl, alkoxy, halogen or cycloalkyl groups or hydrogen. X is either a cycloalkyl group having 6 to 12 C atoms or a linear or branched alkylene group having 1 to 10 C atoms, in which one or two $CH_2$ groups can be replaced by —CH=CH— groups, and where the cycloalkyl group and alkylene group defined above are monosubstituted by a —COOH, C(O)O ($C_1$-$C_6$-alkyl), —C(O)$NH_2$, —C(O)NH($C_1$-$C_6$-alkyl), —C(O)N($C_1$-$C_6$-alkyl)$_2$ or —CN group.

It is the object of the present invention to make available novel compounds which are used as medicaments, where, in particular, use as a c-GMP phosphodiesterase inhibitor is desired. This object is achieved by a compound of the formula

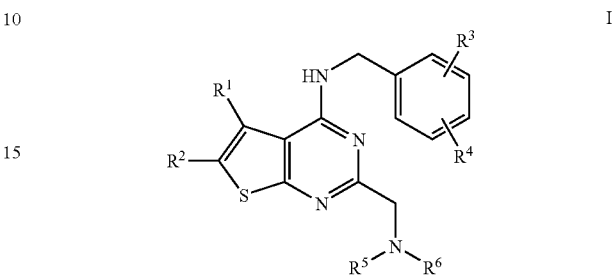

I where
$R^1$, $R^2$ are either identical or different and independently of one another are hydrogen or a linear or branched $C_1$-$C_8$-alkyl group, or, together with the C atoms to which they are bonded, form a 5-7 membered monounsaturated cycloalkenyl ring,
$R^3$, $R^4$ are either identical or different and independently of one another are hydrogen, a hydroxyl group, a linear or branched $C_1$-$C_8$-alkyl group, a $C_1$-$C_8$-alkoxy group or halogen, or together with the C atoms to which they are bonded, form a 5- to 8-membered ring which besides carbon atoms can optionally contain one or more oxygen atoms,
$R^5$, $R^6$ can be identical or different and independently of one another are hydrogen, a linear or branched $C_1$-$C_8$-alkyl group which can be substituted by one or more hydroxyl, $C_1$-$C_8$-alkoxy, amine, mono($C_1$-$C_8$-alkyl)amine, di($C_1$-$C_8$-alkyl)amine, nitrilo, N-morpholino, phenyl, benzodioxole or pyridyl groups or a $C_4$-$C_7$ cycloalkyl group or together with the nitrogen atom to which they are bonded, form a saturated heterocyclic ring which optionally contains one or more further nitrogen and/or oxygen atoms and which is substituted by one or more $C_1$-$C_8$-alkyl, hydroxyl, $C_1$-$C_8$-alkoxy, $C_1$-$C_8$-alkylol, $C_1$-$C_6$-oligohydroxyalkyl, amino, mono($C_1$-$C_8$-alkyl)amino, di($C_1$-$C_8$-alkyl)amino, —$SO_2R^7$ or —C(O)$R^7$ groups,
$R^7$ is a $C_1$-$C_8$-alkyl group, $C_1$-$C_8$-fluoroalkyl group, a phenyl group which is optionally substituted by alkyl, halogen or nitrile groups, or a benzodioxole group.

It has been found that the 2-aminoalkylthieno[2,3-d]pyrimidines of the formula (I) and their physiologically tolerable salts have advantageous pharmacological properties.

In particular, the molecules of the general formula (I) show a specific inhibition of c-GMP phosphodiesterase. These compounds are therefore particularly suitable for the treatment of conditions of the cardiovascular system and the treatment and the therapy of potency disorders which occur in the form of erectile dysfunction.

The determination of the biological activity of the compounds (I) according to the invention is carried out, for example, according to the method which is described in WO 93/06104. In this method, the affinity of the compounds according to the invention for c-GMP and c-AMP phosphodiesterase is determined by the determination of the $IC_{50}$ values. The $IC_{50}$ value here is the concentration of the inhibitor which is needed to give a 50% inhibition of the enzyme activity. The phosphodiesterases used here can be isolated by known methods, which are described, for example, by W. J. Thompson et al. in Biochem. 10, pages 311 ff (1971). The tests can be carried out, for example, by the modified batch method of W. J. Thompson and M. M. Appleman, described in Biochem. 18, pages 5228 ff (1979).

The efficacy of the compounds of the formula (I) according to the invention in the treatment and therapy of potency disorders was demonstrated by inhibition of the phenylephedrine-induced contractions in corpus cavernosum preparations of hares. In this method, the demonstration of the biological activity is advantageously carried out according to the method which is described by F. Holmquist et al. in J. Urol., 150, pages 1310 to 1350 (1993).

Advantageous results were obtained if compounds of the general formula (I) were used in which the radicals $R^1$ to $R^5$ have the meaning indicated below.

The radicals $R^1$, $R^2$ are different, one radical thereof is hydrogen, the other is a linear or branched $(C_1-C_4)$-alkyl group, preferably a methyl or ethyl group, or $R^1$ and $R^2$ together form a propylene, butylene or pentylene group.

The radicals $R^3$ and $R^4$ can be identical or different and are located in positions 3 and 4 of the phenyl ring; they are independently of one another hydrogen, a linear or branched $(C_1-C_6)$alkyl group, a linear or branched $(C_1-C_6)$alkoxy group or halogen, or together form a propylene, butylene, pentylene, ethylenoxy, methylenoxy or ethylenedioxy group.

The radicals $R^5$ and $R^6$ can be identical or different and independently of one another are hydrogen or a $C_1-C_6$-alkyl group which is unsubstituted or substituted by one or more hydroxyl, methoxy, ethoxy, nitrile, methylamine, ethylamine, dimethylamine, diethylamine, pyridyl, benzodioxole or N-morpholino groups, or a cyclopentyl or cyclohexyl group, or $R^5$, $R^6$ form, with the nitrogen atom to which they are bonded, a piperidinyl or piperazinyl ring which is optionally substituted by one or more hydroxyl, hydroxycarbonyl, $C_1-C_2$-alkylamine, an $-SO_2-R^7$ or $-C(O)-R^7$ group, where $R^7$ is a $C_1-C_3$-alkyl group, a $C_1-C_3$-fluoroalkyl group, a phenyl group substituted by one or more alkyl or nitrile groups or a benzodioxole group.

The compounds according to the invention are suitable for use as medicaments, it being possible to prepare both human and veterinary medicaments.

In these uses the compounds according to the invention are frequently employed in the form of their physiologically tolerable salts. Those suitable are generally metal salts, for example alkali metal and alkaline earth metal salts, and ammonium salts, for example of ammonia itself or of organic amines.

Another preferred form of salts in the case of the compounds according to the invention are acid addition salts. These can be prepared using the customary processes known to a person skilled in the art, for example by reaction of the compounds according to the invention with the respective acid in an inert solvent and subsequent isolation of the salt, for example by evaporation. Examples of acids which yield physiologically acceptable salts are, on the one hand, inorganic acids, such as sulphuric acid, nitric acid, hydrohalic acid, for example hydrochloric acid or hydrobromic acid, phosphoric acids, for example orthophosphoric acid, or sulfamic acid.

On the other hand, organic acids also form suitable salts. These are, for example, formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- and ethanesulfonic acid, ethanedisulfonic acid, 2-hydroxyethanesulfonic acid, benzenesulfonic acid, p-toluenesulfonic acid, naphthalenemono- and -disulfonic acids, and laurylsulphuric acid.

For use as medicaments, the compounds according to the invention or their physiologically acceptable salts are formulated to give suitable pharmaceutical preparations. In this process, they are brought into a suitable dose form with at least one suitable vehicle or one excipient, which can be solid, liquid or semi-liquid. Such pharmaceutical preparations are a further subject of the invention.

Suitable vehicles here are the customary organic and inorganic substances known to a person skilled in the art, which are selected according to the intended administration, i.e. enteral, parenteral or topical. General examples of substances of this type are water, vegetable oils, benzyl alcohols, alkylene glycols, polyethylene glycols, glyceryl triacetate, gelatin, carbohydrates, for example lactose or starch, magnesium stearates, talc and petroleum jelly. In the selection of the abovementioned vehicles, care is to be taken here, of course, that these do not react with the substances according to the invention.

Examples of administration forms for oral administration, which is the preferred administration form according to the invention, are, in particular, tablets, pills, coated tablets, capsules, powders, granules, syrups, juices and drops.

In the case of rectal administration, use is made, in particular, of suppositories, and in the case of parenteral administration solutions are used, preferably oily or aqueous solutions, furthermore suspensions, emulsions and implants are also used.

Examples for topical application include ointments, creams and powders.

Another possibility consists in lyophilizing the compounds according to the invention. The lyophilizates can then be used, for example, for the production of injection preparations.

The preparations of the substances according to the invention can be sterilized and/or can contain excipients such as lubricants, preservatives, stabilizers and wetting agents, emulsifiers, salts for influencing the osmotic pressure, buffer substances, colourants and flavourings. Examples of such substances are vitamins.

The dosage of the substances according to the invention is preferably amounts from 1 to 500 mg, in particular 5 to 100 mg, per dose unit. Daily dose units in this case are from 0.02 to 10 mg/kg of body weight. It is true here, however, that the individual dose can vary greatly from patient to patient and also for each individual patient and depends on all sorts of factors. Such factors are, for example, the efficacy of the specific compound employed, age, body weight, general state of health, sex, food taken during the administration period, time of administration and route of administration, excretion rate, pharmaceutical combination and the severity of the particular condition.

The compounds of the formula (I) according to the invention are prepared by reaction of the corresponding 2-halomethylthieno[2,3-d]pyrimidine of the general formula (IIa) with the appropriate alkylamine of the formula (III), as is shown in the following equation (1).

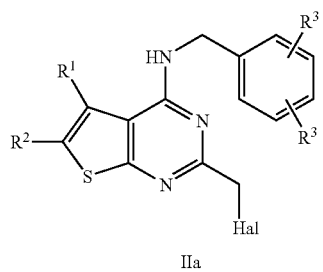 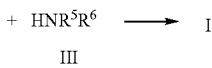

In the formulae (IIa) and (III), the substituents $R^1$ to $R^6$ have the meaning indicated in connection with the formula (I). Hal is a halogen atom, preferably chlorine.

The reaction according to equation (1) is carried out at temperatures from −30 to 150° C., preferably 0 to 120° C. The reaction can in this case be carried out in substance, without use of a solvent, or using a suitable solvent. Those suitable are generally the customary solvents known to a person skilled in the art. Examples are hydrocarbons such as hexane, petroleum ether, benzene, toluene and xylene, chlorinated hydrocarbons such as trichloroethylene, 1,2-dichloroethane, carbon tetrachloride, chloroform and dichloromethane, alcohols such as methanol, ethanol, isopropanol, n-propanol, n-butanol or tert-butanol, ethers such as diethyl ether, diisopropyl ether, tetrahydrofuran and dioxane, glycol ethers such as ethylene glycol monomethyl and monomethyl ethers, ethylene glycol dimethyl ether, ketones such as acetone and butanone, amides such as acetamide, dimethylacetamide, N-methylpyrrolidone and dimethylformamide, nitriles such as acetonitrile, sulfoxides such as dimethyl sulfoxide, nitro compounds such as nitromethane and nitrobenzene, esters such as ethyl acetate, and also mixtures of the abovementioned solvents. Dimethylformamide and/or N-methylpyrrolidone are/is preferably used as a solvent.

After the reaction is complete, the substance obtained is worked up in the customary manner, for example by extraction with an organic solvent after treating with water, and the compound isolated in the customary manner, for example by distilling off the solvent. Generally, the residue obtained is recrystallized for purification.

The 2-halomethylthieno[2,3-d]pyrimidines of the general formula (IIa) can be prepared from the corresponding 4-chlorothienopyrimidines by reaction with the appropriate, optionally substituted benzylamine. The description of an analogous reaction, in which the pyrimidine ring is substituted by a group X, as was defined in the formula (II) above, instead of with a halomethyl function is given in the Applicant's German application with the reference 196 44 228. The reaction conditions disclosed there can be transferred to the substances of the present invention.

The 4-chlorothienopyrimidines can be obtained in a manner known from the literature, see, for example, Houben-Weyl, Methoden der organischen Chemie, Georg Thieme Verlag, Stuttgart.

The invention is now illustrated in greater detail in the following examples. The temperatures here are indicated in ° C., and the abbreviations have the meaning known to a person skilled in the art. All products were in this case worked up after reaction was complete by adding water and the pH of the solution was adjusted to values between about 2 and 10, depending on the product obtained. Extraction was then carried out with ethyl acetate or dichloromethane, and the organic phase was separated off and dried. The solvent was then removed by distillation and the residue obtained was purified by chromatography on silica gel and/or crystallization.

EXAMPLE 1

A solution of 2 g of 4-(3-chloro-4-methoxybenzylamino)-2-chloromethyl-5,6,7,8 tetrahydrobenzothieno[2,3-d]pyrimidine in 10 ml of DMF is treated with 5 ml of 3-aminopropanol and heated at 80° for one hour. It is then diluted with water and extracted with ethyl acetate. The crystalline product obtained after customary work-up is dissolved in alcoholic HCl and treated with ether until turbidity. 2.1 g of 4-(3-chloro-4-methoxybenzylamino)-2-(3-hydroxypropylaminomethyl)-5,6,7,8-tetrahydrobenzothieno[2,3-d]pyrimidine are obtained in the form of its dihydrochloride.

M.p.=225°.

EXAMPLE 2

The reaction was carried out as described in Example 1, an equivalent amount of diethamolamine being used instead of 3-aminopropanol.

After treating with the respective acid, 4-(3-chloro-4-methoxybenzylamino)-2-(bis-2-hydroxyethylaminomethyl)-5,6,7,8-tetrahydrobenzothieno[2,3-d]pyrimidine was then obtained in the form of its hydrochloride.

M.p.=180°.

EXAMPLE 3

The reaction was carried out as described in Example 1, an equivalent amount of 4-piperidinol being used instead of 3-aminopropanol.

After treating with the respective acid, 4-(3-chloro-4-methoxybenzylamino)-2-(4-hydroxypiperidinomethyl)-5,6,7,8-tetrahydrobenzothieno[2,3-d]pyrimidine was then obtained in the form of its dihydrochloride.

M.p.=119°.

EXAMPLE 4

The reaction was carried out as described in Example 1, an equivalent amount of 3-methoxypropylamine being used instead of 3-aminopropanol.

After treating with the respective acid, 4-(3-chloro-4-methoxybenzylamino)-2-(3-methoxypropylaminomethyl)-5,6,7,8-tetrahydrobenzothieno[2,3-d]pyrimidine was then obtained in the form of its dihydrochloride.

M.p.=116°.

EXAMPLE 5

The reaction was carried out as described in Example 1, an equivalent amount of 2-hydroxyethylamine being used instead of 3-aminopropanol.

After treating with the respective acid, 4-(3-chloro-4-methoxybenzylamino)-2-(2-hydroxyethylaminomethyl)-5,6,7,8-tetrahydrobenzothieno[2,3-d]pyrimidine was then obtained in the form of its dihydrochloride.

M.p.=225°.

EXAMPLE 6

The reaction was carried out as described in Example 1, an equivalent amount of N,N-dimethyltrimethylenediamine being used instead of 3-aminopropanol.

After treating with the respective acid, 4-(3-chloro-4-methoxybenzylamino)-2-(N, N-dimethylaminopropylaminomethyl)-5,6,7,8-tetrahydrobenzothieno-[2,3-d]pyrimidine was then obtained in the form of its 1,5-fumarate.

M.p.=180°.

EXAMPLE 7

The reaction was carried out as described in Example 1, an equivalent amount of N-hydroxyethylpiperazine being used instead of 3-aminopropanol.

After treating with the respective acid, 2-{4-[4-(3-chloro-4-methoxybenzylamino)-5,6,7,8-tetrahydrobenzo[4,5]thieno[2,3-d]pyrimidin-2-ylmethyl]piperazin-1-yl}ethanol was then obtained in the form of its dihydrochloride.

The following were obtained analogously:

1-{4-[4-(3-Chloro-4-methoxybenzylamino)-5,6,7,8-tetrahydrobenzo-[4,5]thieno[2,3-d]pyrimidin-2-ylmethyl]piperazin-1-yl}-2,2,2-trifluoroethanone
1-{4-[4-(3-Chloro-4-methoxybenzylamino)-5,6,7,8-tetrahydrobenzo-[4,5]thieno[2,3-d]pyrimidin-2-ylmethyl]piperazin-1-yl}ethanone
(3-Chloro-4-methoxybenzyl)[2-(4-methanesulfonylpiperazin-1-ylmethyl-5,6,7,8-tetrahydrobenzo[4,5]thieno[2,3-d]pyrimidin-4-yl]amine
1-[4-(3-Chloro-4-methoxybenzylamino)-5,6,7,8-tetrahydrobenzo-[4,5]thieno[2,3-d]pyrimidin-2-ylmethyl]piperidin-3-ol
(3-Chloro-4-methoxybenzyl)(2-{[(pyridin-2-ylmethyl)amino]methyl}-5,6,7,8-tetrahydrobenzo[4,5]thieno[2,3-d]pyrimidin-4-yl)amine
1-Benzo[1,3]dioxol-5-yl-1-{4-[4-(3-chloro-4-methoxybenzylamino)-5,6,7,8-tetrahydrobenzo[4,5]thieno[2,3-d]pyrimidin-2-ylmethyl]piperazin-1-yl}-methanone
4-(1-{4-[4-(3-Chloro-4-methoxybenzylamino-5,6,7,8-tetrahydrobenzo-[4,5]thieno[2,3-d]pyrimidin-2-ylmethyl]piperazin-1-yl}methanoyl)-benzonitrile
(3-Chloro-4-methoxybenzyl){2-[4-(toluene-4-sulfonyl)piperazin-1-ylmethyl]-5,6,7,8-tetrahydrobenzo[4,5]thieno[2,3-d]pyrimidin-4-yl}amine
4-{4-[4-(3-Chloro-4-methoxybenzylamino)-5,6,7,8-tetrahydrobenzo-[4,5]thieno[2,3-d]pyrimidin-2-ylmethyl]piperazine-1-sulfonyl}benzonitrile
(2-{[(Benzo[1,3]dioxol-5-ylmethyl)amino]methyl}-5,6,7,8-tetrahydrobenzo[4,5]thieno[2,3-d]pyrimidin-4-yl)(3-chloro-4-methoxybenzyl)amine
3-{[4-(3-Chloro-4-methoxybenzylamino)-5,6,7,8-tetrahydrobenzo-[4,5]thieno[2,3-d]pyrimidin-2-ylmethyl]amino}propane-1,2-diol
(3-Chloro-4-methoxybenzyl){2-[(2-morpholin-4-ylethylamino)methyl]-5,6,7,8-tetrahydrobenzo[4,5]thieno[2,3-d]pyrimidin-4-yl}amine
3-{4-[4-(3-Chloro-4-methoxybenzylamino)-5,6,7,8-tetrahydrobenzo-[4,5]thieno[2,3-d]pyrimidin-2-ylmethyl]piperazin-1-yl}propane-1,2-diol
(3-Chloro-4-methoxybenzyl)[2-(4-dimethylaminopiperidin-1-ylmethyl)-5,6,7,8-tetrahydrobenzo[4,5]thieno[2,3-d]pyrimidin-4-yl]amine
6-{[4-(3-Chloro-4-methoxybenzylamino)-5,6,7,8-tetrahydrobenzo-[4,5]thieno[2,3-d]pyrimidin-2-ylmethyl]amino}hexan-1-ol
(3-Chloro-4-methoxybenzyl)(2-cyclohexylaminomethyl-5,6,7,8-tetrahydrobenzo[4,5]thieno[2,3-d]pyrimidin-4-yl)amine
1-[[4-(3-Chloro-4-methoxybenzylamino)-5,6,7,8-tetrahydrobenzo-[4,5]thieno[2,3-d]pyrimidin-2-ylmethyl](2-hydroxypropyl)amino]propan-2-ol
3-[[4-(3-Chloro-4-methoxybenzylamino)-5,6,7,8-tetrahydrobenzo-[4,5]thieno[2,3-d]pyrimidin-2-ylmethyl](2-cyanoethyl)amino]propionitrile (2S,3S,4S,5R)-6{[4-(3-Chloro-4-methoxybenzylamino)-5,6,7,8-tetrahydrobenzo[4,5]thieno[2,3-d]pyrimidin-2-ylmethyl]methylamino}hexane-1,2,3,4,5-pentaol The following examples relate to pharmaceutical preparations:

EXAMPLE A: INJECTION VIALS

A solution of 100 g of an active compound of the formula (I) and 5 g of disodium hydrogenphosphate is adjusted to pH 6.5 in 3 l of double-distilled water using 2 N hydrochloric acid, dispensed into injection vials, lyophilized under sterile conditions and aseptically sealed. Each injection vial contains 5 mg of active compound.

EXAMPLE B: SUPPOSITORIES

A mixture of 20 g of an active compound of the formula (I) is fused with 100 g of soya lecithin and 1400 g of cocoa butter, poured into moulds and allowed to cool. Each suppository contains 20 mg of active compound.

EXAMPLE C: SOLUTION

A solution is prepared from 1 g of an active compound of the formula (I), 9.38 g of $NaH_2PO_4.2H_2O$, 28.48 g of $Na_2HPO_4.12H_2O$ and 0.1 g of benzalkonium chloride in 940 ml of double-distilled water. The solution is adjusted to pH 6.8, made up to 1 l and sterilized by irradiation. This solution can be used in the form of eye drops.

EXAMPLE D: OINTMENT 500 g of an active compound of the formula (I) are mixed with 99.5 g of petroleum jelly under aseptic conditions.

EXAMPLE E: TABLETS

A mixture of 1 kg of active compound of the formula (I), 4 kg of lactose, 1.2 kg of potato starch, 0.2 kg of talc and 0.1 kg of magnesium stearate is compressed in a customary manner to give tablets such that each tablet contains 10 mg of active compound.

EXAMPLE F: COATED TABLETS

Analogously to Example E, tablets are pressed and are then coated in a customary manner with a coating of sucrose, potato starch, talc, tragacanth and colourant.

EXAMPLE G: CAPSULES 2 kg of active compound of the formula (I) are filled into hard gelatin capsules in a customary manner such that each capsule contains 20 mg of the active compound.

EXAMPLE H: AMPOULES

A solution of 1 kg of active compound of the formula (I) in 60 l of double-distilled water is sterile filtered, dispensed into ampoules, lyophilized under sterile conditions and aseptically sealed. Each ampoule contains 10 mg of active compound.

EXAMPLE I: INHALATION SPRAY 14 g of active compound of the formula (I) are dissolved in 10 ml of isotonic NaCl solution and the solution is filled into commercially available spray containers having a pump mechanism. The solution can be sprayed into the mouth or nose. One puff of spray (approximately 0.1 ml) corresponds to a dose of approximately 0.14 mg.

What is claimed is:

1. Compound of the formula (I)

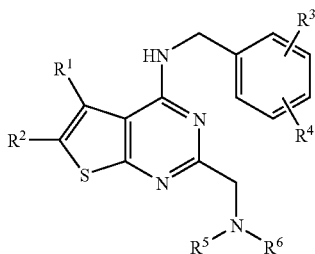

I where
R$^1$, R$^2$ are either identical or different and independently of one another are hydrogen or a linear or branched C1-C8-alkyl group, or together with the C atoms to which they are bonded, form a 5 to 7-membered monounsaturated cycloalkenyl ring, R$^3$, R$^4$ are either identical or different and independently of one another are hydrogen, a hydroxyl group, a linear or branched C$_1$-C$_8$-alkyl group, a C$_1$-C$_8$-alkoxy group or halogen, or together with the C atoms to which they are bonded, form a 5- to 8-membered ring which besides carbon atoms can optionally contain one or more oxygen atoms, R$^5$, R$^6$ can be identical or different and independently of one another are hydrogen, a linear or branched C$_1$-C$_8$-alkyl group which can be substituted by one or more hydroxyl, C$_1$-C$_8$-alkoxy, amine, mono(C$_1$-C$_8$-alkyl)amine, di(C$_1$-C$_8$-alkyl)amine, nitrilo, N-morpholino, phenyl, benzodioxole or pyridyl groups, or a C$_4$-C$_7$-cycloalkyl group, or together with the nitrogen atom to which they are bonded, form a saturated heterocyclic ring which optionally contains one or more further nitrogen and/or oxygen atoms and which is substituted by one or more C$_1$-C$_8$-alkyl, hydroxyl, C$_1$-C$_8$-alkoxy, C$_1$-C$_8$-alkylol, C$_1$-C$_6$-oligohydroxyalkyl, amino, mono (C$_1$-C$_8$-alkyl)amino, di(C$_1$-C$_8$-alkyl)amino, —SO$_2$R$^7$ or —C(O)R$^7$ groups, R$^7$ is a C$_1$-C$_8$-alkyl group, C$_1$-C$_8$-fluoroalkyl group, a phenyl group which is optionally substituted by alkyl, halogen or nitrile groups or a benzodioxole group.

2. Compound according to claim 1, wherein:
R$^1$, R$^2$ are different and one radical is hydrogen and the other is selected from the group consisting of linear and branched (C$_1$-C$_4$)alkyl groups, or R$^1$ and R$^2$ together form a propylene, butylene or pentylene group, R$^3$ and R$^4$ are identical or different and are located in positions 3 and 4 of the phenyl ring; they are independently of one another hydrogen, a linear or branched (C$_1$-C$_6$)alkyl group, a linear or branched (C$_1$-C$_6$)alkoxy group or halogen, or together form a propylene, butylene, pentylene, ethylenoxy, methylenoxy or ethylenedioxy group, R$^5$ and R$^8$ are identical or different and independently of one another are hydrogen or a C$_1$-C$_6$-alkyl group which is unsubstituted or substituted by one or more hydroxyl, methoxy, ethoxy, nitrile, methylamine, ethylamine, dimethylamine, diethylamine, pyridyl, benzodioxole or N-morpholino groups, or a cyclopentyl or cyclohexyl group, or R$^5$, R$^6$ form, together with the nitrogen atom to which they are bonded, a piperidinyl or piperazinyl ring which is optionally substituted by one or more hydroxyl, hydroxycarbonyl, C$_1$-C$_2$-alkylamine, —SO$^2$—R$^7$ or —C(O)—R$^7$ groups, where R$^7$ is a C$_1$-C$_3$-alkyl group, a C$_1$-C$_3$-fluoroalkyl group, a phenyl group substituted by one or more alkyl or nitrile groups or a benzodioxole group.

3. A compound of claim 1, which is: 4-(3-Chloro-4-methoxybenzylamino)-2-(3-hydroxypropylaminomethyl)-5,6,7,8-tetrahydrobenzothieno[2,3-d]pyrimidine, 4-(3-Chloro-4-methoxybenzylamino)-2-(bis-2-hydroxyethylaminomethyl)-5,6,7,8-tetrahydrobenzothieno[2,3-d]pyrimidine, 4-(3-Chloro-4-methoxybenzyl-amino)-2-(bis-4-hydroxypiperidinomethyl)-5,6,7,8-tetrahydrobenzothieno[2,3-d]pyrimidine, 4-(3-Chloro-4-methoxybenzylamino)-2-(3-methoxypropylaminomethyl)-5,6,7,8-tetrahydrobenzothieno[2,3-d]-pyrimidine, 4-(3-Chloro -4-methoxybenzylamino)-2-(2-hydroxyethylaminomethyl)-5,6,7,8-tetrahydrobenzothieno [2,3-d]pyrimidine, 4-(3-Chloro-4-methoxybenzylamino)-2-(N,N-dimethylaminopropylaminomethyl)-5,6,7,8-tetrahydrobenzothieno[2,3-d]pyrimidine, 1-{4-[4-(3-Chloro-4-methoxybenzylamino)-5,6,7,8-tetrahydrobenzo[4,5]thieno-[2,3-d]pyrimidin-2-ylmethyl]piperazin-1-yl}-2,2,2-trifluoroethanone, 1-{4-[4-(3-Chloro-4-methoxybenzylamino)-5,6,7,8-tetrahydrobenzo[4,5]thieno[2,3-d]pyrimidin-2-ylmethyl] piperazin-1-yl}ethanone, (3-Chloro-4-methoxybenzyl)[2-(4-methanesulfonylpiperazin-1-ylmethyl)-5,6,7,8-tetrahydrobenzo[4,5]thieno [2,3-d]pyrimidin-4-yl]-amine, 1-[4-(3-Chloro-4-methoxybenzyiamino)-5,6,7,8-tetrahydrobenzo[4,5]thieno[2,3-d]pyrimidin -2-ylmethyl]piperidin-3-ol, (3-Chloro-4-methoxybenzyl)(2-{[(pyridin-2-ylmethyl) amino]methyl}-5,6,7,8-tetrahydrobenzo[4,5]thieno[2,3-d]pyrimidin-4-yl)amine, 1-Benzo[1,3]dioxol-5-yl-1-{4-[4-(3-chloro-4-methoxybenzylamino)-5,6,7,8-tetrahydrobenzo[4,5]thieno[2,3-d]pyrimidin-2-ylmethyl]-piperazin-1-yl}methanone, 4-(1-{4-[4-(3-Chloro-4-methoxybenzylamino)-5,6,7,8-tetrahydrobenzo[4,5]thieno[2,3-d]pyrimidin-2-ylmethyl]piperazin-1-yl}-methanoyl)benzonitrile, (3-Chloro-4-methoxybenzyl){2-[4-(toluene-4-sulfonyl) piperazin-1-ylmethyl]-5,6,7,8-tetrahydrobenzo[4,5] thieno[2,3-d]pyrimidin-4-yl}-amine, 4-{4-[4-(3-Chloro-4-methoxybenzylamino)-5,6,7,8-tetrahydrobenzo[4,5]thieno[2,3-d]pyrimidin-2-ylmethyl] piperazine-1-sulfonyl}-benzonitrile, (2-{[(Benzo[1,3]dioxol-5-ylmethyl)amino]methyl}5,6,7,8-tetrahydrobenzo[4,5]thieno[2,3-d]pyrimidin-4-yl)(3-chloro-4-methoxybenzyl)-amine,
3-{[4-(3-Chloro-4-methoxybenzylamino)-5,6,7,8-tetrahydrobenzo[4,5]thieno[2,3-d]pyrimidin-2-ylmethyl]amino}propane-1,2-diol,
(3-Chloro-4-methoxybenzyl){2-[(2-morpholin-4-ylethylamino)methyl]-5,6,7,8-tetrahydrobenzo[4,5]thieno[2,3-d]pyrimidin-4-yl}amine,
3-{4-[4-(3-Chloro-4-methoxybenzylamino)-5,6,7,8-tetrahydrobenzo[4,5]thieno[2,3-d]pyrimidin-2-ylmethyl]piperazin-1-yl}propane-1,2-diol,
(3-Chloro-4-methoxybenzyl)-[2-(4-dimethylaminopiperidin-1-ylmethyl)-5,6,7,8-tetrahydrobenzo[4,5]thieno[2,3-d]pyrimidin-4-yl]-amine,
6-{[4-3-Chloro-4-methoxybenzylamino)-5,6,7,8-tetrahydrobenzo[4,5]thieno[2,3-d]pyrimidin-2-ylmethyl]amino}hexan-1-ol,
(3-Chloro-4-methoxybenzyl)(2-cyclohexylaminomethyl-5,6,7,8-tetrahydrobenzo[4,5]thieno[2,3-d]pyrimidin-4-yl)amine,
1-[[4-(3-Chloro-4-methoxybenzylamino)-5,6,7,8-tetrahydrobenzo[4,5]thieno[2,3-d]pyrimidin-2-ylmethyl](2-hydroxypropyl)amino]-propan-2-ol,
3-[[4-(3-Chloro-4-methoxybenzylamino)-5,6,7,8-tetrahydrobenzo[4,5]thieno[2,3-d]pyrimidin-2-ylmethyl](2-cyanoethyl)amino]-propionitrile,
(2S,3S,4S,5R)-6-{[4-(3-chloro-4-methoxybenzylamino)-5,6,7,8-tetrahydrobenzo[4,5]thieno[2,3-d]pyrimidin-2-ylmethyl]methylamino}-hexane-1,2,3,4,5-pentaol
or one of their physiologically acceptable salts.

4. Medicament comprising a compound according to claim 1 or one of its physiologically acceptable salts.

5. Medicament of claim 4, comprising a compound from the group consisting of
4-(3-Chloro-4-methoxybenzylamino)-2-(3-hydroxypropylaminomethyl)-5,6,7,8-tetrahydrobenzothieno[2,3-d]pyrimidine, 4-(3-Chloro-4-methoxybenzylamino)-2-(bis-2-hydroxyethylaminomethyl)-5,6,7,8-tetrahydrobenzothieno[2,3-d]pyrimidine, 4-(3-Chloro-4-methoxybenzylamino)-2-(bis-4-hydroxypiperidinomethyl)-5,6,7,8-tetrahydrobenzothieno[2,3-d]pyrimidine, 4-(3-Chloro-4-methoxybenzylamino)-2-(3-methoxypropylaminomethyl)-5,6,7,8-tetrahydrobenzothieno[2,3-d]pyrimidine, 4-(3-Chloro -4-methoxybenzylamino)-2-(2-hydroxyethylaminomethyl)-5,6,7,8-tetrahydrobenzothieno[2,3-d]pyrimidine, 4-(3-Chloro-4-methoxybenzylamino)-2-(N,N -dimethylaminopropylaminomethyl)-5,6,7,8-tetrahydrobenzothieno[2,3-d]pyrimidine, 1-{4-[4-(3-Chloro-4-methoxybenzylamino)-5,6,7,8-tetrahydrobenzo[4,5]thieno-[2,3-d]pyrimidin-2-ylmethyl]piperazin-1-yl}2,2,2-trifluoroethanone,
1-{4-[4-(3-Chloro-4-methoxybenzylamino)-5,6,7,8-tetrahydrobenzo[4,5]thieno[2,3-d]pyrimidin-2-ylmethyl]piperazin-1-yl}ethanone,
(3-Chloro-4-methoxybenzyl)[2-(4-methanesulfonylpiperazin-1-ylmethyl)-5,6,7,8-tetrahydrobenzo[4,5]thieno[2,3-d]pyrimidin-4-yl]-amine,
1-[4-(3-Chloro-4-methoxybenzylamino)-5,6,7,8-tetrahydrobenzo[4,5]thieno[2,3-d]pyrimidin-2-ylmethyl]piperidin-3-ol,
(3-Chloro-4-methoxybenzyl)(2-{[(pyridin-2-ylmethyl)amino]methyl}5,6,7,8-tetrahydrobenzo[4,5]thieno[2,3-d]pyrimidin-4-yl)amine, 1-Benzo[1,3]dioxol-5-yl-1-{4-[4-(3-chloro-4-methoxybenzylamino)-5,6,7,8-tetrahydrobenzo[4,5]thieno[2,3-d]pyrimidin-2-ylmethyl]-piperazin-1-yl}methanone,
4-(1-{4-[4-(3-Chloro-4-methoxybenzylamino)-5,6,7,8-tetrahydrobenzo[4,5]thieno[2,3-d]pyrimidin-2-ylmethyl]piperazin-1-yl}methanoyl)benzonitrile,
(3-Chloro-4-methoxybenzyl){2-[4-(toluene-4-sulfonyl) piperazin -1-ylmethyl]-5,6,7,8-tetrahydrobenzo[4,5]thieno[2,3-d]pyrimidin-4-yl}amine,
4-{4-[4-(3-Chloro-4-methoxybenzylamino)-5,6,7,8-tetrahydrobenzo[4,5]thieno[2,3-d]pyrimidin-2-ylmethyl]piperazine-1-sulfonyl}benzonitrile,
(2-{[(Benzo[1,3]dioxol-5-ylmethyl)amino]methyl}5,6,7,8-tetrahydrobenzo[4,5]thieno[2,3-d]pyrimidin-4-yl)(3-chloro-4-methoxybenzyl)amine,
3{[4-(3-Chloro-4-methoxybenzylamino)-5,6,7,8-tetrahydrobenzo[4,5]thieno[2,3-d]pyrimidin-2-ylmethyl]amino}propane-1,2-diol,
(3-Chloro-4-methoxybenzyl){2-[(2-morpholin-4-ylethylamino)methyl]-5,6,7,8-tetrahydrobenzo[4,5]thieno[2,3-d]pyrimidin-4-yl}amine,
3-{4-[4-(3-Chloro-4-methoxybenzylamino)-5,6,7,8-tetrahydrobenzo [4,5]thieno[2,3-d]pyrimidin-2-ylmethyl]piperazin-1-yl}propane-1,2-diol,
(3-Chloro-4-methoxybenzyl)[2-(4-dimethylaminopiperidin-1-ylmethyl)-5,6,7,8-tetrahydrobenzo[4,5]thieno[2,3-d]pyrimidin-4-yl]-amine,
6-{[4-3-Chloro-4-methoxybenzylamino)-5,6,7,8-tetrahydrobenzo[4,5]thieno[2,3-d]pyrimidin-2-ylmethyl]amino}hexan-1-ol,
(3-Chloro-4-methoxybenzyl)(2-cyclohexylaminomethyl-5,6,7,8-tetrahydrobenzo[4,5]thieno[2,3-d]pyrimidin-4-yl)amine,
1-[[4-(3-Chloro-4-methoxybenzylamino)-5,6,7,8-tetrahydrobenzo[4,5]thieno[2,3-d]pyrimidin-2-ylmethyl](2-hydroxypropyl)amino]-propan-2-ol,
3-[[4-(3-Chloro-4-methoxybenzylamino)-5,6,7,8-tetrahydrobenzo[4,5]thieno[2,3-d]pyrimidin-2-ylmethyl](2-cyanoethyl)amino]-propionitrile,
(2S,3S,4S,5R)-6-{[4-(3-Chloro-4-methoxybenzylamino)-5,6,7,8-tetrahydrobenzo[4,5]thieno[2,3-d]pyrimidin-2-ylmethyl]methylamino}hexane-1,2,3,4,5-pentaol
or one of their physiologically acceptable salts.

6. Process for the preparation of a compound according to claim 1, comprising reacting a 2-halomethylthieno[2,3-d]pyrimidine of the formula (IIa)

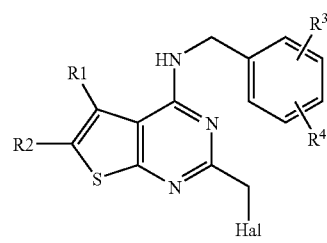

in which the substituents R¹ to R⁴ have the meaning indicated in claim 1, with an alkylamine of the formula (III)

$$HNR^5R^6 \qquad \text{III}$$

in which the substituents R⁵ and R⁶ have the meaning indicated in claim 1, and the substance obtained is optionally purified.

7. Process for the production of a medicament, comprising bringing a compound according to claim 1 or one of its physiologically acceptable salts into a suitable dose form with at least one suitable excipient or vehicle.

8. A method for treating erectile dysfunction which comprises administering to a patient in need thereof a compound according to claim 1.

* * * * *